United States Patent [19]

Rosenfeldt et al.

[11] Patent Number: 5,566,676
[45] Date of Patent: Oct. 22, 1996

[54] PRESSURE DATA ACQUISITION DEVICE FOR A PATIENT MONITORING SYSTEM

[75] Inventors: Bernd Rosenfeldt, Hamilton; Kenneth Fuchs, Wayland; Robert R. Addiss, Bedford, all of Mass.

[73] Assignee: Siemens Medical Systems, Inc., Iselin, N.J.

[21] Appl. No.: 989,416

[22] Filed: Dec. 11, 1992

[51] Int. Cl.[6] .................................................. A61B 5/02
[52] U.S. Cl. ............................................. 128/672; 128/668
[58] Field of Search ...................... 364/413.03; 128/672, 128/675, 705, 710, 712, 903

[56] References Cited

U.S. PATENT DOCUMENTS

| | | |
|---|---|---|
| 3,848,582 | 11/1974 | Milani et al. |
| 3,858,576 | 1/1975 | Dehnert et al. |
| 3,868,679 | 2/1975 | Arneson ................................. 128/673 |
| 4,245,650 | 1/1981 | Wilker et al. |
| 4,249,538 | 2/1981 | Musha et al. |
| 4,325,385 | 4/1982 | Holte . |
| 4,356,475 | 10/1982 | Neumann et al. |
| 4,356,486 | 10/1982 | Mount ................................ 340/870.38 |
| 4,378,021 | 3/1983 | Strand . |
| 4,576,181 | 3/1986 | Wallace ................................. 128/675 |
| 4,577,639 | 3/1986 | Simon et al. |
| 4,606,352 | 8/1986 | Geddes et al. |
| 4,695,955 | 9/1987 | Faisandier ......................... 364/413.03 |
| 4,715,385 | 12/1987 | Cudahy et al. |
| 4,724,844 | 2/1988 | Rafelson . |
| 4,779,199 | 10/1988 | Yoneda et al. |
| 4,858,615 | 8/1989 | Meinema ................................. 128/668 |
| 4,873,654 | 10/1989 | Alexander et al. ................. 364/551.01 |
| 4,895,161 | 1/1990 | Cudahy et al. |
| 4,924,871 | 5/1990 | Honeyager ............................. 128/672 |
| 4,966,154 | 10/1990 | Cooper et al. |
| 4,970,900 | 11/1990 | Shepherd et al. ........................ 73/756 |
| 5,006,835 | 4/1991 | Griswold et al. ........................ 340/626 |
| 5,012,411 | 4/1991 | Policastro et al. ................. 364/413.06 |
| 5,025,808 | 6/1991 | Hafner . |
| 5,029,590 | 7/1991 | Allain et al. |
| 5,036,856 | 8/1991 | Thornton . |
| 5,343,869 | 9/1994 | Pross et al. ............................ 128/700 |

FOREIGN PATENT DOCUMENTS

| | | |
|---|---|---|
| 0466272A1 | 7/1991 | European Pat. Off. . |
| 524992 | 12/1969 | Switzerland . |
| WO81/02832 | 10/1981 | WIPO . |

OTHER PUBLICATIONS

Hewlett Packard brochure: "Patient Data Management System–System Discription," Manual Part No. 78707-91998-9, Jan. 1982.

Marquette Electronics, Inc. brochure: "Unity Monitoring Network–The Power of Integrated Patient Monitoring, 1990".

J. Webster, "Encyclopedia of Medical Devices and Instrumentation, vol. 3", pp. 2016–2025, John Wiley and Sons 1988.

Corometrics Medical Systems, Inc. brochure: Neotrak 515A Neonatal Monitoring System, 1982.

Siemens Medical Systems Inc. brochure: "System Sirecust Lim Cartridge", order #A91004-M3331-G091-05-7600.

Baxter Health Care Corp., Edwards Critical Care division "SAT-2" publication No. 687-8/89-CC, Aug. 1989, p. 3.

*Primary Examiner*—Angela D. Sykes
*Assistant Examiner*—Bryan Yarnell
*Attorney, Agent, or Firm*—Lawrence C. Edelman

[57] ABSTRACT

A data acquisition device is disclosed for use in a patient monitoring system which includes a display device. The system also includes a pressure transducer which produces patient blood pressure signals. The data acquisition device includes terminals for receiving signals representing blood pressure from the pressure transducer. Circuitry in the data acquisition device, including multiplexers and a digital to analog converter conditions the signals representing blood pressure. The pressure transducer and the circuitry are collocated. The device also includes circuit paths for electrically coupling the pressure transducer and the conditioning circuitry. The conditioning circuitry is selectably coupled to the display to provide the conditioned signals to the display. The data acquisition device may be positioned independently of the display device.

18 Claims, 7 Drawing Sheets

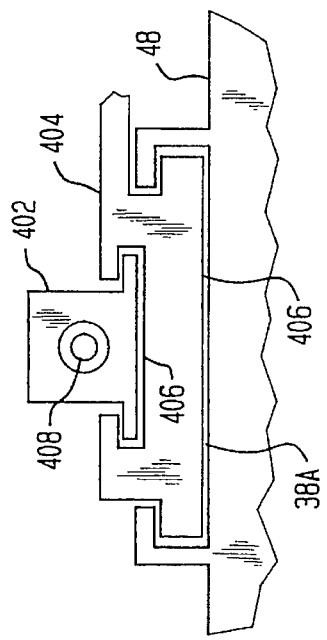
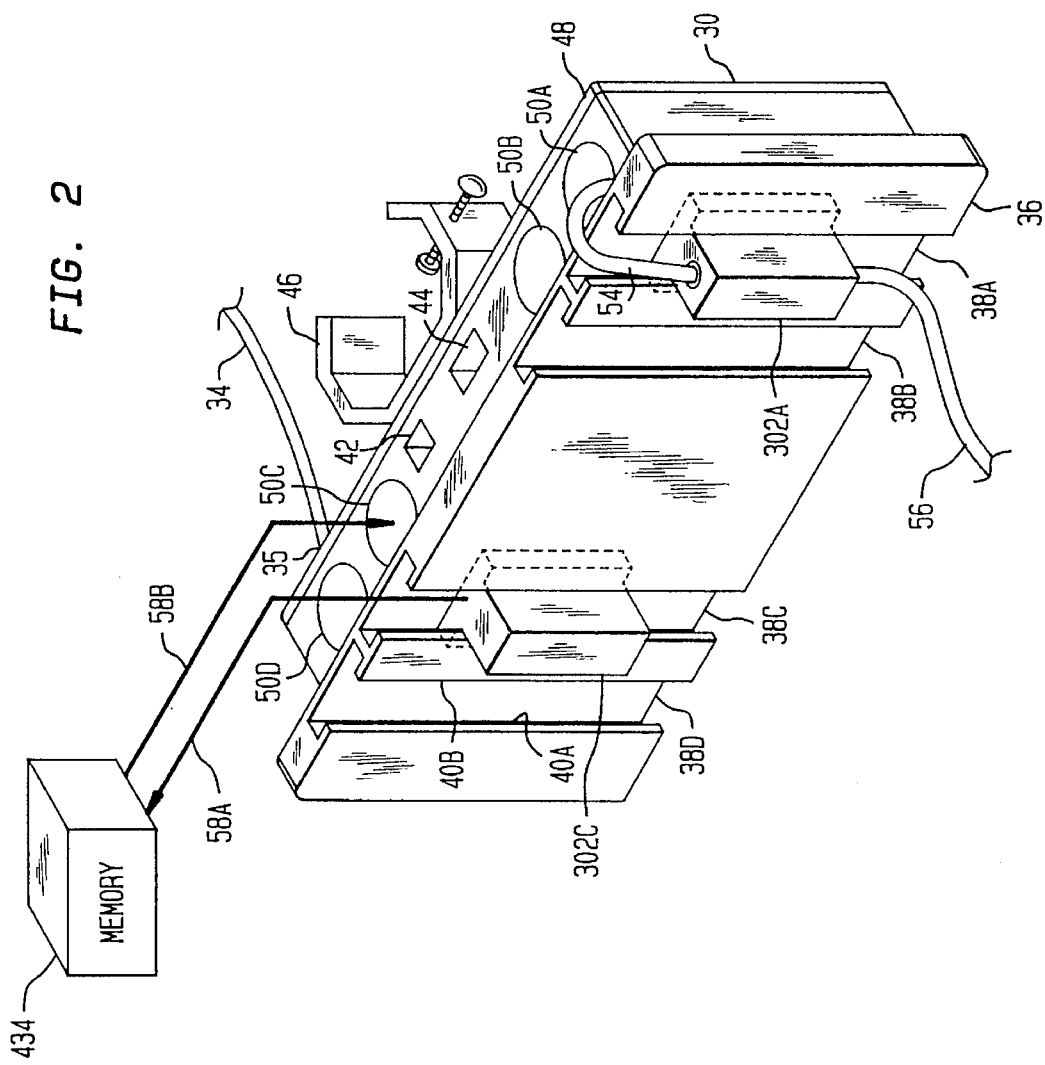

PRESSURE DATA ACQUISITION DEVICE FOR A PATIENT MONITORING SYSTEM

CROSS REFERENCE TO RELATED APPLICATIONS

The following U.S. applications which are assigned to the same assignee as the instant application and filed concurrently therewith have related subject matter:

U.S. Ser. No. 07/988,989 entitled TRANSPORTABLE MODULAR PATIENT MONITOR; U.S. Ser. No. 07/989,414 entitled DATA ACQUISITION POD FOR A PATIENT MONITORING SYSTEM; Ser. No. 07/989,410 entitled DOCKING STATION FOR A PATIENT MONITORING SYSTEM; and U.S. Ser. No. 07/989,415 entitled TRANSPORTABLE MODULAR PATIENT MONITOR WITH DATA ACQUISITION MODULES.

BACKGROUND OF THE INVENTION

1. Field of the Invention

The present invention relates to medical systems and in particular to patient monitoring systems for collecting, storing and displaying medical data pertaining to the patient.

2. Description of the Related Art

In hospitals and other health care environments, it is often necessary to continually collect and analyze a variety of medical data pertaining to a patient. These data may include electrocardiogram signals, body temperature, blood pressure, respiration, pulse and other monitored vital signs.

Monitoring systems in the related art have typically fallen into one of two general categories: multi-function monitoring, recording and displaying systems which process and collect all of the data desired, but are bulky and difficult to transport; and small, portable systems which are easy to transport, but process and collect fewer types of data and have limited storage capability. Initially (e.g., in an ambulance or an emergency room) a patient is connected to a simple, portable monitor to observe a limited number of medical attributes, such as EKG or non-invasive blood pressure. As the patient moves to higher care facilities (e.g., an intensive care unit or operating room) it is desirable to augment these simple monitors to observe additional parameters. Generally, this is accomplished by disconnecting the patient from the simple monitor and connecting the patient to a monitoring system having more robust capabilities.

The need for continuity of data collection and display is most pressing in emergency situations. Hospital personnel want to monitor additional parameters, change the selection of parameters viewed, or retrieve trend data from the patient's history. At the same time, the patient may have to move to a different care unit. During an emergency, the speed at which a patient is transferred from a bed to an operating room or intensive care unit may substantially impact the patient's chance of survival. Accordingly, hospital personnel need to be able to quickly add functionality to the patient monitoring system and/or to quickly transfer the patient to a high performance care unit.

Two major considerations in the design of monitoring systems have been ease and speed of system reconfiguration. It is particularly undesirable to connect sensors to a patient or to disconnect them immediately prior to transportation or administration of critical procedures. U.S. Pat. Nos. 4,715,385 and 4,895,385 to Cudahy et al. discuss a monitoring system which includes a fixed location display unit and a portable display unit. A digital acquisition and processing module (DAPM) receives data from sensors attached to the patient and provides the data to either or both of the fixed and portable display units. The DAPM remains attached to the patient during patient transport, eliminating the need to remove intrusive devices from the patient before transport and to reconnect the devices after transport. Normally, the DAPM is inserted into a bedside display unit located near the patient's bed. An electrical connection to the bedside display is formed when the DAPM is inserted into the bedside display. In order to place the DAPM in the bedside monitor, sufficient cable length is provided between the sensors and the DAPM to reach the bedside display unit.

To enable insertion of the DAPM into the bedside monitor, the lines transmitting the analog data signals from the patient to the DAPM are long enough to reach from the patient to the bedside monitor. This cable length may allow the analog signals to be corrupted with noise due to, for example, radio frequency interference (RFI) from external sources.

Furthermore, the digital acquisition and processing module of the Cudahy et al. system has a fixed parameter configuration, and if the parameter requirements change due to a change in condition of the patient, the digital acquisition and processing module must be disconnected and a different module including the new parameters which are required to be monitored must be connected. This process is not only time consuming, due to the reconnection of the sensors and cables between the patient and the module, but also destructive of data, since patient data acquired in the first processing module is lost when that module is disconnected. Furthermore, the processing module of Cudahy et al. is bulky and, so, difficult to position near a patient. In addition, the Cudahy et al. processing module requires extensive cabling to the different patient sensors, which further adds to the complexity and set-up time of the system and makes it more difficult to care for the patient.

Besides the time delays which may be encountered when adding sensors to the monitor configuration, systems in the prior art also leave much to be desired with respect to cable management. As the number of sensors attached to the patient grows, so does the number of wires between the patient and the monitoring means. This network of wires makes it difficult to navigate the space around the patient's bed. Data acquisition modules or cartridges for collection of blood pressure data from invasive sensors (e.g., those using a catheter) have an additional disadvantage. Each pressure transducer is coupled to the patient by a hose which conveys fluid, and the transducer is coupled to monitoring means by an electrical wire. The transducers are desirably positioned at the height of the patient's heart to properly measure pressure in the right or left atrium. If the patient's position changes, transducer height must follow the patient's heart to maintain the accuracy of the measurements.

One solution to the problem of positioning the transducer is disclosed in European patent application No. 91201792.8 by van den Berg. This application describes a junction box adapted to receive four pressure transducers, on the outside surface. The wires from each transducer extend into the junction box. A single cable with a multiple connector plug (multiplug) extends out of the junction box and is coupled to monitor means. A clamp provides means for adjusting the height of the transducers.

Another problem with pressure data acquisition apparatus has been the location of the controls for calibrating the blood pressure transducers. In most currently available systems, these controls are located on the monitoring means, remote from the transducers. To calibrate the transducers in a prior art system, the operator must expose the transducers to atmospheric pressure. Then the operator must walk around the wires to the monitor in order to reset the pressure value displayed on the monitor to zero. Then the operator must walk back around the wires to the transducers and close them off against the atmosphere. This is a time consuming procedure. To solve this problem, some systems have included foot pedal controls coupled to the monitor, to enable the operator to send a pressure zero signal to the monitor while working at the patient's bedside.

A similar problem has been experienced when measuring pulmonary artery wedge pressure. To measure wedge pressure, a catheter having a small inflatable balloon at its tip is passed into the pulmonary artery. The balloon is inflated and the catheter is swept by blood flow further into the pulmonary artery where it wedges, obstructing blood flow. The pressure between the balloon and the left atrium (across the pulmonary capillaries and pulmonary vein) falls off to match the left atrial pressure. Typically, the controls to initiate wedge pressure measurement have been located at the monitor. To initiate the measurement, the operator must position the balloon catheter in the patient and inflate the balloon. Then the operator must then walk around the wires to the monitor and actuate the wedge start switch.

Another aspect of prior art data acquisition devices is that they are not standalone devices. An example is the Sirecust™ cartridge system manufactured by Siemens Medical Equipment. In this system, patient medical data are collected by one or more multiparameter cartridges. In order to display the data, the cartridges are inserted into a SIREM™ module box. The large size of the module box makes it impractical to place the box on or above the bed; it typically must be placed beside the bed, and may get in the way of hospital personnel who are treating the patient. Not only is the box in the way, but as noted above, an array of cables between the cartridge and the patient further interferes with movement of hospital personnel. The Hewlett-Packard Merlin™ system and the Marquette TRAM™ systems are similar in that they also require insertion of a cartridge into a module box to display data on a bedside monitor. The Cudahy patent has a similar limitation: the DAPM must be inserted into the fixed (bedside) display to display data collected by the DAPM. None of these is a standalone device.

Additional simplification is desired, in order to reduce the network of wiring and hoses surrounding the patient. Simplification of the controls for operating pressure data acquisition transducers is also desirable.

SUMMARY OF THE INVENTION

The present invention is embodied in a data acquisition device for use in a patient monitoring system which includes a display device. The system also includes a pressure transducer which produces patient blood pressure signals. The data acquisition device includes an input port at which signals representing blood pressure are received from the pressure transducer. The data acquisition device also includes circuitry which conditions the signals received from the transducer. The pressure transducer and the conditioning means are collocated. The data acquisition device is electrically coupled to the pressure transducer and to the display device. The data acquisition device located in a position remote from the display device.

BRIEF DESCRIPTION OF THE FIGURES

FIG. 2 is a perspective drawing of the data acquisition device shown in FIG. 1.

FIG. 3 is a top plan view of a transducer holder which may be mounted on the data acquisition device shown in FIG. 2.

DESCRIPTION OF THE EXEMPLARY EMBODIMENTS

OVERVIEW

Figure 1:
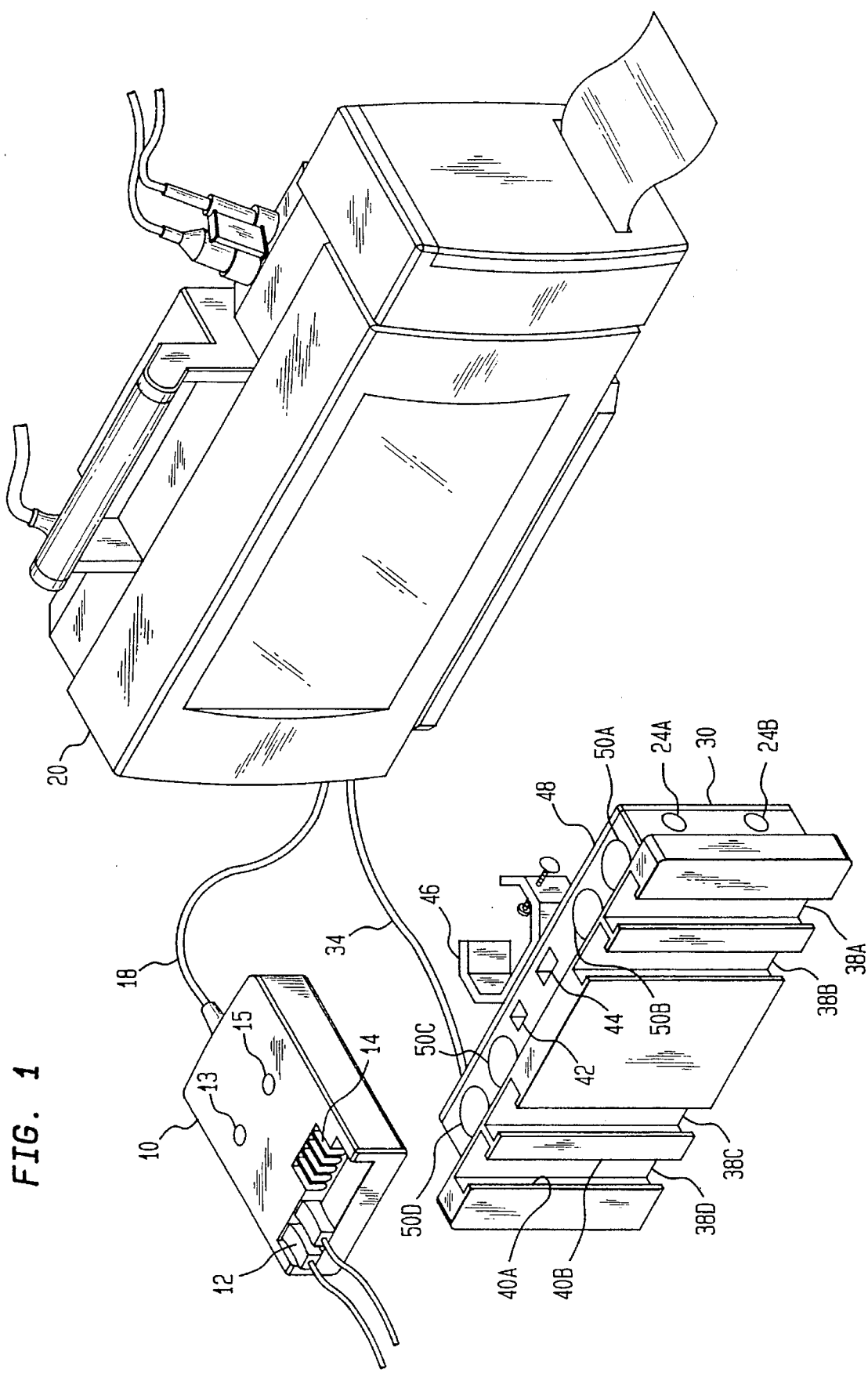
FIG. 1 is a perspective drawing of a system which includes a data acquisition device in a accordance with the invention.

FIG. 1 shows a system which includes an exemplary data acquisition device 30 in accordance with the invention. Device 30 is configured to receive data representing blood pressure or both blood pressure and temperature. The device may be placed on a bed or a bedside table. Alternatively it may be attached to the bed, an intravenous pole or a dedicated stand.

The data acquisition device is selectively and detachably coupled, by a single coupling line 34, to a display 20, which may be a portable display line 34 plugs into a port 35 of device 30. If for any reason, it is desirable to replace display 20 with a further selected display (not shown), this may be accomplished by detaching coupling line 34 from the display 20, and attaching the line 34 to the new display. Another data acquisition device 10 is also shown. Device 30 may be used alone or in combination with another device such as device 10, for monitoring multiple parameters in a data acquisition system. Device 10 may include a plurality of terminals 14 which are coupled, for example, to EKG electrodes. The device 10 may also include a plurality of terminals 12 which are coupled to resistance sensors such as temperature, nasal respiration or cardiac output thermodilution sensor leads by a plurality of receiving lines 16. Device 30 may be positioned independently of device 10, and of display 20. Device 30 is small enough in size to be conveniently located close to the patient.

Data acquisition device 30 includes a housing 48 and means for detachably mounting the housing 48 to an external structure, such as an intravenous (IV) pole, a bed rail, a post, or a dedicated stand. The mounting means may be in the form of a clamp 46, a hook, a velcro fastener, or other known fastener. The clamp 46 allows rapid adjustment of the height of data acquisition device 30 when the patient's position is changed. The clamp 46 also allows the user to rapidly detach data acquisition device 30 when the patient is transported.

FIG. 2 is an enlarged view of device 30. The sensors, or pressure transducers, are collocated with the data acquisition electronics, contained in a housing, and are mounted on the housing, proximate to the electronics. Only two transducers 302a and 302c are shown in FIG. 2. The other two transducers (not shown) may be identical and are mounted in a the same manner. In the exemplary embodiment, the transducers are mounted on the front surface of housing 48. Each pressure transducer is inserted into one of four channels 38a–38d on the front surface of housing 48. Channels 38a–38d provide a means for detachably mounting the transducers to housing 48. Each pressure transducer includes a short cable 54 which is inserted into a connector 50a–50d. Connectors 50a–50d receive electrical signals representing pressure from the transducers. Each of the cables 54 transmits these signals from a respective transducer 302a–302d to the data acquisition electronics inside device 30. Connectors 50a–50d are collocated with respective mounting channels 38a–38d, to minimize the length of the cable 54 used to electrically couple the pressure transducers with the connectors 50a–50d.

Alternative methods of mounting the transducers may also be used. For example, the transducers may be mounted in a detachable transducer holder 404, a portion of which is shown in FIG. 3. Holder 404 is separate from data acquisition device 30. Holder 404 may have up to four members 406 adapted to fit into mounting channels 38a–38d of housing 48. Holder 404 includes three additional transducer channels (not shown) identical to channel 406 to receive three additional transducers (not shown), which may be identical to transducer 402. As shown in FIG. 3, adapter 404 is configured to receive a transducer 402 which is smaller than channel 38a. It is understood by one skilled in the art that adapter 404 may be constructed to receive transducers of any size, and may have a transducer channel 406 which is larger or smaller than the mounting channel 38a.

The use of a separate transducer holder 404 may be advantageous in a hospital where transducers of different sizes are procured from multiple sources. A single data acquisition device 30 may then be used in conjunction with any of these transducers. The hospital need only procure an additional holder having a transducer channel of the appropriate size for any new transducer 402.

Another alternative mounting method (not shown) simplifies the connection of the transducers to the data acquisition electronics. In this method, each channel 38a–38d includes electrodes 40a and 40b for contacting electrodes on the surface of the transducers. Electrical and mechanical couplings are simultaneously established by inserting the transducers into their respective channels. There is no need to connect separate cables to connectors 50a–50d.

Figure 4:
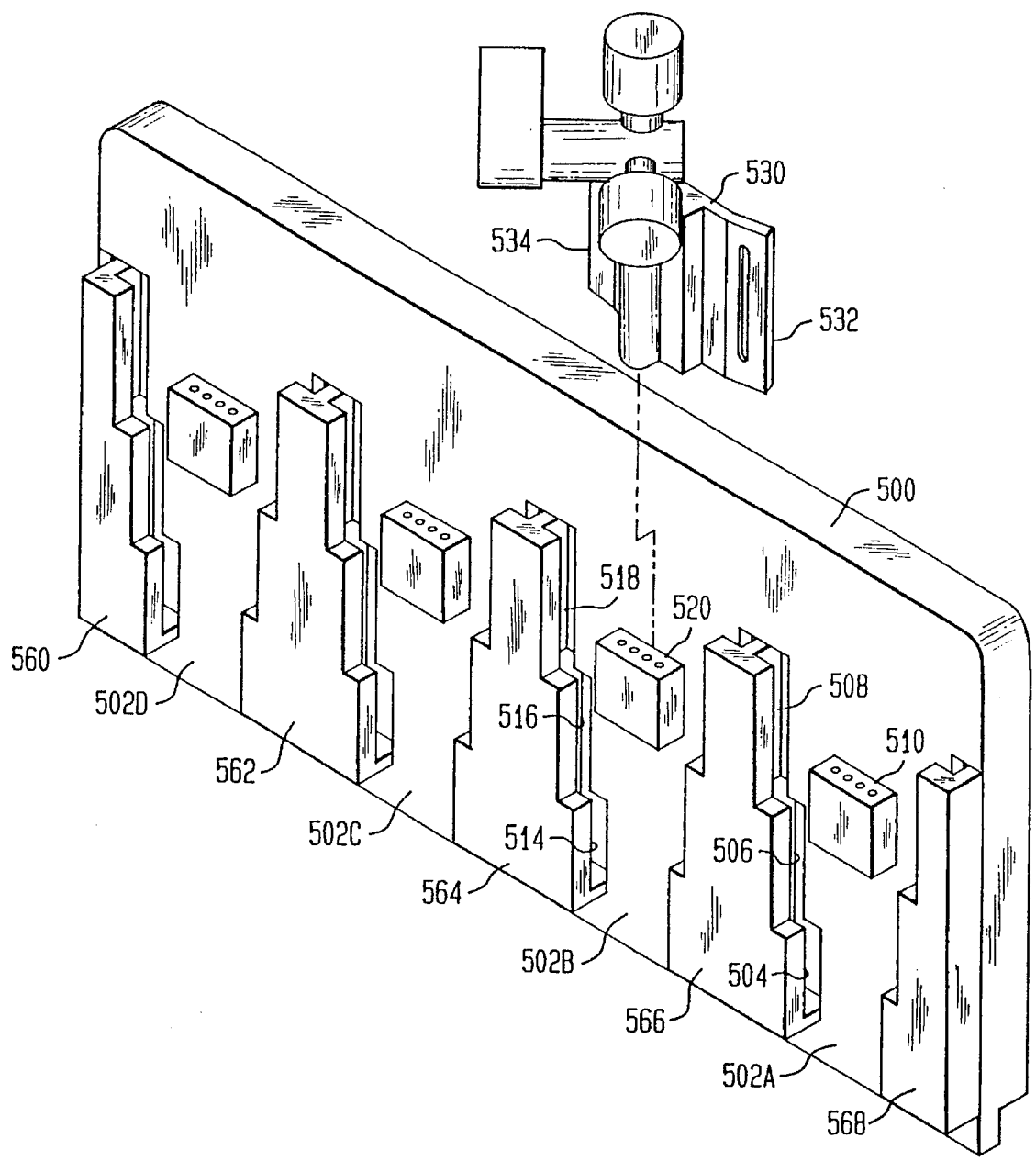
FIG. 4 is a perspective view of an alternative holder which may be used to couple multiple transducers to a data acquisition device such as that shown in FIG. 1.
Figure 5:
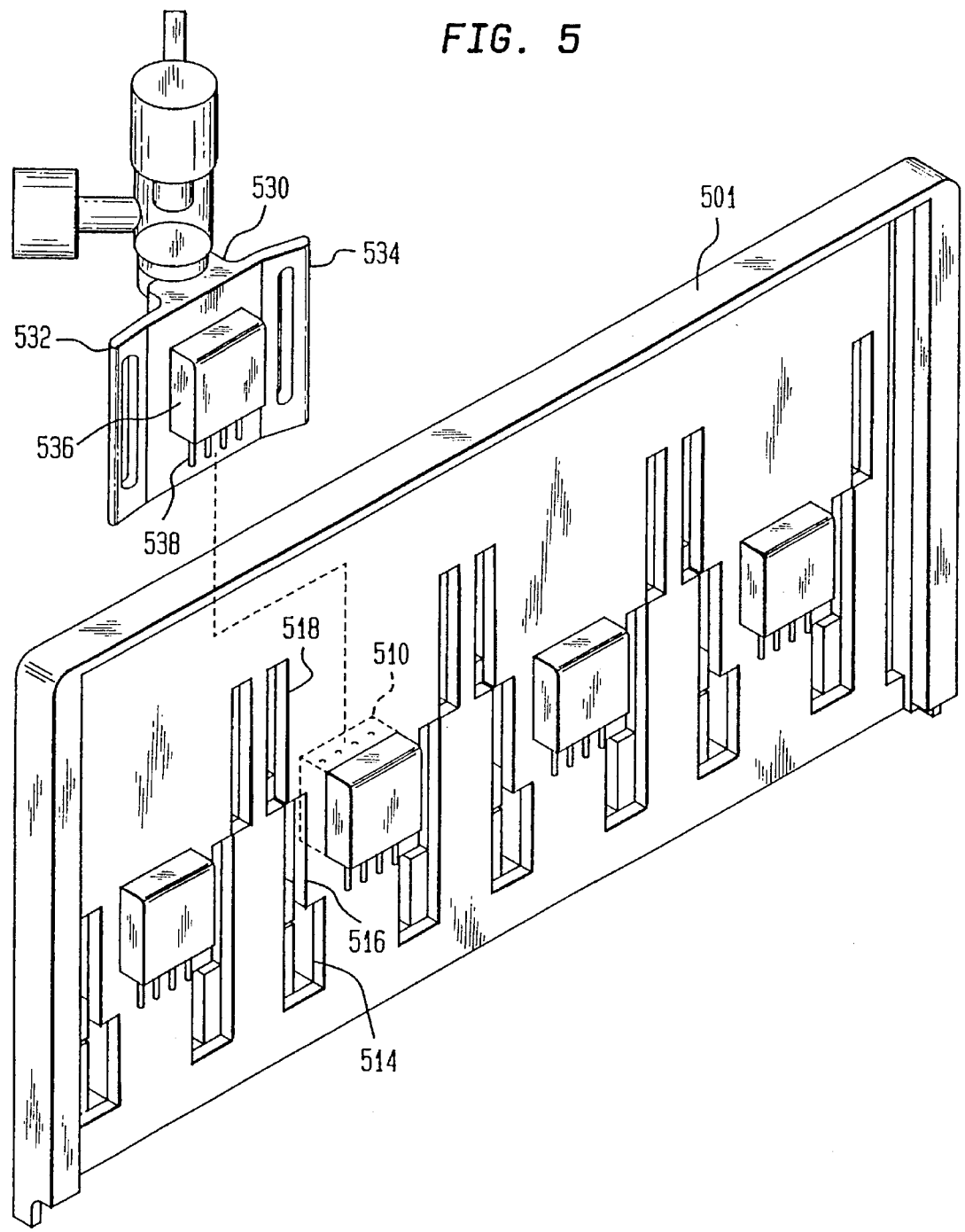
FIG. 5 is a rear perspective view of the holder shown in FIG. 4.

Still another means for mounting transducers is shown in FIGS. 4 and 5. FIG. 4 shows the front plate 500 of an alternative embodiment of the device housing. Plate 500 has five raised members 560, 562, 564, 566 and 568 which form four variable width channels 502a–502d. Each channel 502a–502d includes three distinct sections (e.g., sections 504, 506, and 508 of channel 502a). Each section is sized to receive a pressure transducer 530 having mounting plates 532 and 534 of a predetermined width. Each channel 502a–502d includes a feed-through connector 510 (shown as a female connector) for mating with a connector 536 (as shown in FIG. 5) on pressure transducer 530.

Plate 500 may be molded of a suitable plastic material and may be molded without any holes for receiving connector 510. A rectangular hole may be subsequently stamped in at one of the three sections 514, 516 or 518 of channels 502a–502d. With this single hole, plate 500 is then dedicated for use with a transducer having a size to fit in the channel section 514, 516, or 518 adjacent the hole, as shown in FIGS. 4 and 5. Alternatively, plate 500 may have three holes (not shown), each hole adjacent a respective section 514, 516 and 518 of channel 502a–502d.

Referring to FIG. 5, a rear view of a plate 501 is shown. Plate 501 is similar to plate 500, except that the hole which receives connector 510 is located adjacent channel section 516 instead of section 518 as shown in FIG. 4. The connector 536 on transducer 530 includes pins 538 for mating with connector 510 on plate 501. Preferably, the transducer 530 has the male connector and plate 501 has the female connector. This configuration is preferred, because the pins 538 of the male connector are more prone to damage than the female connector. Transducer 530 is disposable, so it is cost effective to locate the pins on disposable transducer 530; although it is understood that transducer 530 could have a female connector and connector 510 could be male.

Referring again to FIG. 1, device 30 includes 2 input ports 24a and 24b for receiving temperature data from invasive temperature sensors.

As shown in FIG. 1, unlike the data acquisition cartridges known in the prior art, data acquisition device 30 is a preconfigured, standalone (self contained) unit. As a preconfigured device, device 30 includes all of the electronics required to receive the analog electrical signals, representing pressure measurements, from the pressure transducers, filter and clamp the signals, combine them into a single analog signal and convert the single analog signal into a digital output signal. This digital output signal may be transferred directly to display device 20 by wire 34 or by a wireless (e.g., infrared) link (not shown). As a standalone device (unlike the prior art cartridges), device 30 is neither inserted into a bulky box or rack, nor into the display device itself, to form an electrical path to the display device. Using the data acquisition electronics described below with reference to FIGS. 6 and 7, device 30 may be formed in a small enough package to be conveniently placed in a variety of locations in close proximity to the patient.

Reducing the size of device 30 so that it is selectably positionable near the patient is advantageous because it reduces the length of the hose 56 which connects the catheter in the patient to the transducer. The shorter the hose, the less likely it is to become twisted, bent or kinked, which could cause incorrect measurements. A shorter hose is also less likely to be accidentally jostled, struck or pulled, enhancing safety for the hose, the transducer, device 30 and most importantly, the patient.

Data acquisition device 30 also has two control switches conveniently located on housing 48: a pressure zero switch 42 and a wedge start switch 44. During a calibration operation, the fluid inlets to the respective transducers are opened up to atmospheric pressure (by disconnecting the hose), pressure zero switch 42 is then actuated by the operator. This causes device 30 to send a signal to display device 20. This pressure zero signal causes display device 20 to zero the pressure waveform on the display. Once the reference voltage is reset, the hose 56 which is connected to the patient is reconnected to the pressure transducer.

By locating pressure zero switch 42 on device 30, proximate to the transducers, the logistics of calibrating the transducers are simplified. Once the transducers are exposed to atmospheric pressure, the operator can actuate switch 42 without walking over to the display device 20, and without walking around the hoses 56 and wire 34. The calibration is quicker, easier and safer.

Similarly, the pulmonary artery wedge pressure measurement operation is simplified. When measuring wedge pressure, the operator performs the catheter insertion and balloon inflation near the patient. Then the operator actuates switch 44 to start the wedge pressure measurement. Actuating switch 44 causes device 30 to transmit a wedge start signal to display device 20. The wedge start signal causes the display device to initiate a wedge pressure measurement, i.e., to display the data signals it receives using coefficients and processing parameters appropriate for wedge pressure measurement. Again, the operator does not need to walk over to the monitor, or walk around any hoses or wires to start the measurement.

Another advantage of having the transducers close to the electronics (mounted on the housing 48) is that the electrical paths between the transducers and the electronics are short, so as to reduce radio frequency (RF) interference. The noise added to each signal prior to amplification is reduced by shortening the electrical path over which the signal travels before amplification. Noise and signal transport artifacts are avoided, which would otherwise occur if the amplification were performed further from the patient and, even in the absence of external noise sources, if the impedances of the couplings to the patient were imbalanced. The signals are converted to digital form in an A/D converter (not shown) in the pod electronics before being transmitted across the comparatively long coupling line 34 between the data acquisition device 30 and the display device 20. Once converted to digital form, the data are less vulnerable to corruption due to crosstalk between signals and to RFI. Although a line 34 is shown, the detachable coupling between the data acquisition device 30 and display device 20 is intended to include any manner of communicating the acquired data signals to display device 20, such as a wireless communication link (not shown), which may be an infrared link.

DETAILED DESCRIPTION

Figure 6:
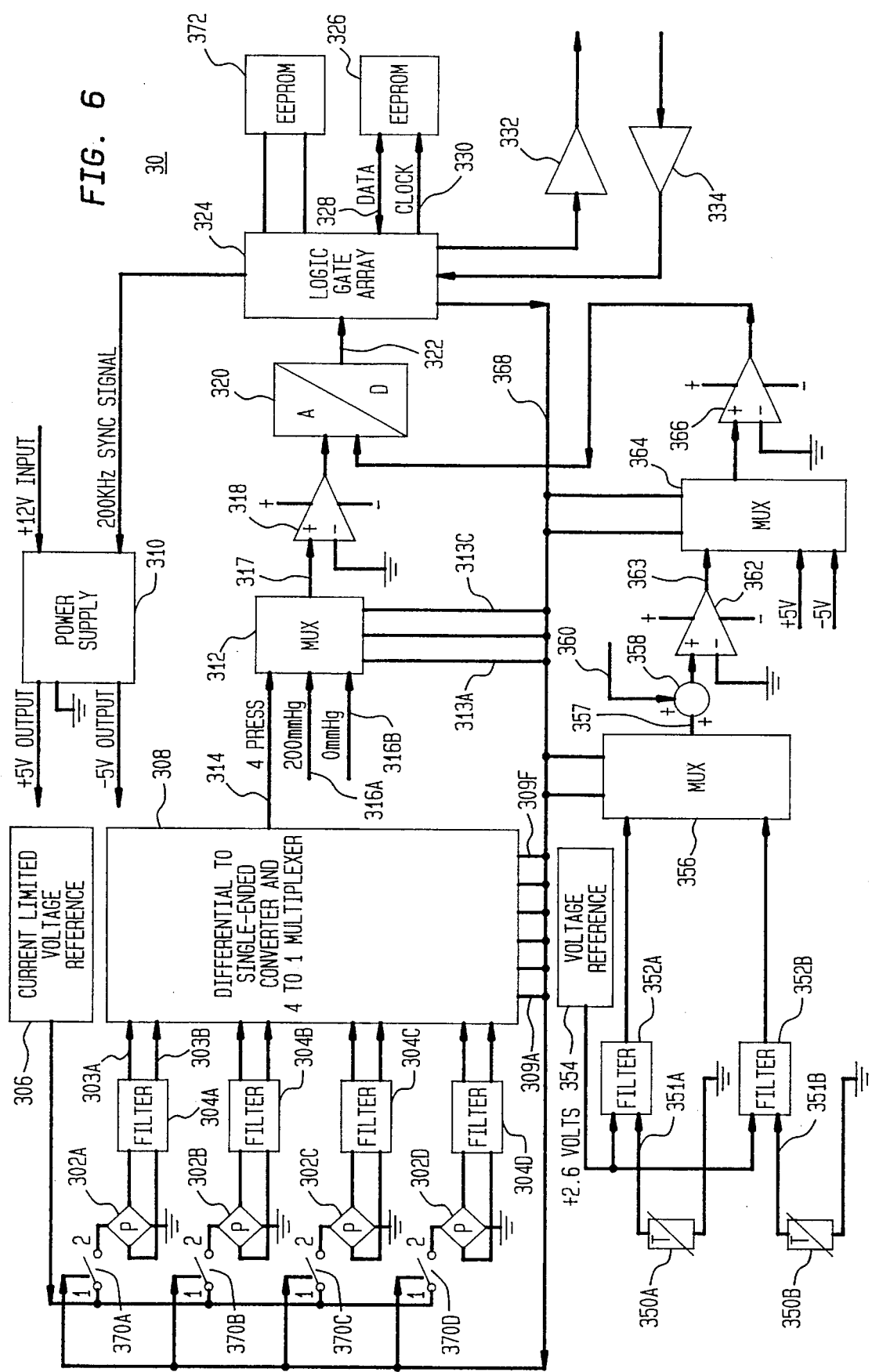
FIG. 6 is a functional block diagram, partly in schematic diagram form of the data acquisition device shown in FIG. 2.

FIG. 6 is a block diagram of the pressure/temperature data acquisition device 30 shown in FIG. 2. The device 30 receives data from up to four pressure transducers 302a–302d and two temperature transducers 350a and 350b. Power is provided by a single step-down power supply 310. The output signals from the transducers 302a–302d are provided to respective clamping and filtering networks 304a–304d, to limit the dynamic range of the signals and remove noise.

The output signals 303a, 303b from each of the networks 304a–304d are provided to a differential-to-single-ended converter and 4-to-1 multiplexer 308. The differential-to-single-ended converter 308 generates a single signal 314 representative of pressure difference from each pair of signals 303a and 303b.

Instead of applying an excitation voltage to all four transducers with continuous DC voltage (i.e., applying power to the resistive bridge element inside all four transducers), power is applied to one transducer at a time in a pulsed fashion. A switch 370a closes and applies power to one of the transducers 302a. A capacitor (not shown in FIG. 6) within converter 308 charges up to a differential voltage which is proportional to the pressure in transducer 302a. (Transducer 302a has a bridge output signal which is differential in nature). Subsequently, switch 370a is opened again and power to transducer 302a is turned off. The voltage is trapped in the internal capacitor converter 308, representing the output signal of the transducer. Subsequently, successive switches 370b–370d are individually closed to apply power to respective pressure transducers 302b–302d in succession.

An advantageous aspect of this configuration is that power is conserved, relative to a system in which the excitation voltage is applied to all four transducers simultaneously. In the exemplary embodiment of the invention, four transducers are used, consuming no more power than is required to operate one transducer continuously. It is particularly valuable to reduce power consumption if the data acquisition device is intended for use in conjunction with a portable display such as display device 20, with limited battery capacity. This feature allows operational transducers to continue to operate even when one transducer fails with an electrical short.

The output signals from networks 304b–304d are converted to pressure difference signals. The converter 308 is controlled by signals 309a–309f sent over a timing bus 368. The timing bus 368 also controls the transducers, so that converter 308 acts as a time division multiplexer, transmitting signals representing the output signals of the respective transducers in round robin fashion.

The output signal 314 is multiplexed together with reference pressure signals 316a, 316b in multiplexer 312. Multiplexer 312 is controlled by signals 313a–313c which are received from the timing bus 368. The signal 317 is boosted by amplifier 318 so that it occupies a range of values coextensive with the input range of the A/D converter 320, which converts it to digital form. The digital output data signal 322 is Manchester encoded in a logic gate array 324 and is sent out to the display device 20 by data transmitter 332.

Logic 324 controls the timing for activating transducers 302a–302d by closing respective switches 370a–370d, for converting differential voltage to single-ended voltage in converter 308, and for multiplexing the output signals from converter 308.

Another function of logic 324 is to respond to actuation of either one of pressure zero switch 42 and wedge pressure switch 44. When one of the switches 42 and 44 is actuated, logic 324 causes device 30 to transmit a respective pressure zero signal or a wedge start signal to display device 20. Logic 324 may be implemented in application specific integrated circuits (ASIC), or using programmable array logic (PAL).

A memory device, which may be a conventional electrically erasable programmable read only memory (EEPROM) 326 is provided for local storage of calibration coefficients and/or alarm limits which may be used by gate array 324. A data receiver 334 receives commands from the display device 20. A second memory device, which may also be an EEPROM 372 stores permanent data, such as the serial number or revision level of a printed circuit board. It is understood by those skilled in the art that this memory may be located outside of housing 48 (as shown by memory 434 in FIG. 2) of blood pressure pod 30, and may be connected to pod 30. Memory 434 may be selectively detachable from pod 30. A single memory 434 is shown coupled to transducer 302c. Similar memories may be coupled to each transducer. If each transducer has a respective memory, it is convenient to allow the memories to accompany the transducers when the patient moves. Thus, if a department does not wish to allow its pod 30 to accompany the patient to another part of the hospital (e.g., out of fear that the device will not return), memory 434 may be detached from pod 30 and may be connected to another, equivalent pod for transportation to a different part of the hospital. This provides an additional element of flexibility in selectively coupling devices 30 to display device 20.

By storing these data in device 30, exchanging equipment (e.g., substituting another display for display device 20) is simplified. Pod 30 may be disconnected from display device 20 and reconnected to another display without the need for time consuming data downloads from display device 20 to the other display.

The output signals 351a and 351b from respective temperature transducers, 350a and 350b, are filtered and clamped by circuits 352a and 352b, to remove noise and to limit the signal range. The filtered signals are provided to multiplexer 356, which produces a single TDM signal 357. An offset signal 360 is added to the TDM signal 357 in adder 358, and the resulting signal is boosted in amplitude by amplifier 362. The amplified signal 363 is multiplexed together with plus and minus five volt monitor signals provided by the step down power supply 310 in multiplexer 364. The power supply monitor signals are provided to allow deviations from the nominal five volt operational power signal provided by power supply 310 to be detected. The multiplexer output signal is then boosted by amplifier 366 and the resulting signal is provided to A/D converter 320. The temperature data is provided to the logic gate array 324 where it is Manchester encoded and transmitted to the display.

The capacitor 378 is accessed by differential multiplexer 308. The input signal to multiplexer 308 is differential. The output signal 314 of multiplexer 308 is differential, except that one of the differential output lines of multiplexer 308 is coupled to ground. One electrode of the capacitor is coupled to ground through multiplexer 308. As soon as multiplexer 308 accesses the capacitor, the capacitor output signal changes from a differential voltage to a single ended voltage. The output signal 314 is thus a single ended voltage referenced to ground. This signal may be sensed by a single ended amplifier such as amplifier 318.

Figure 7:
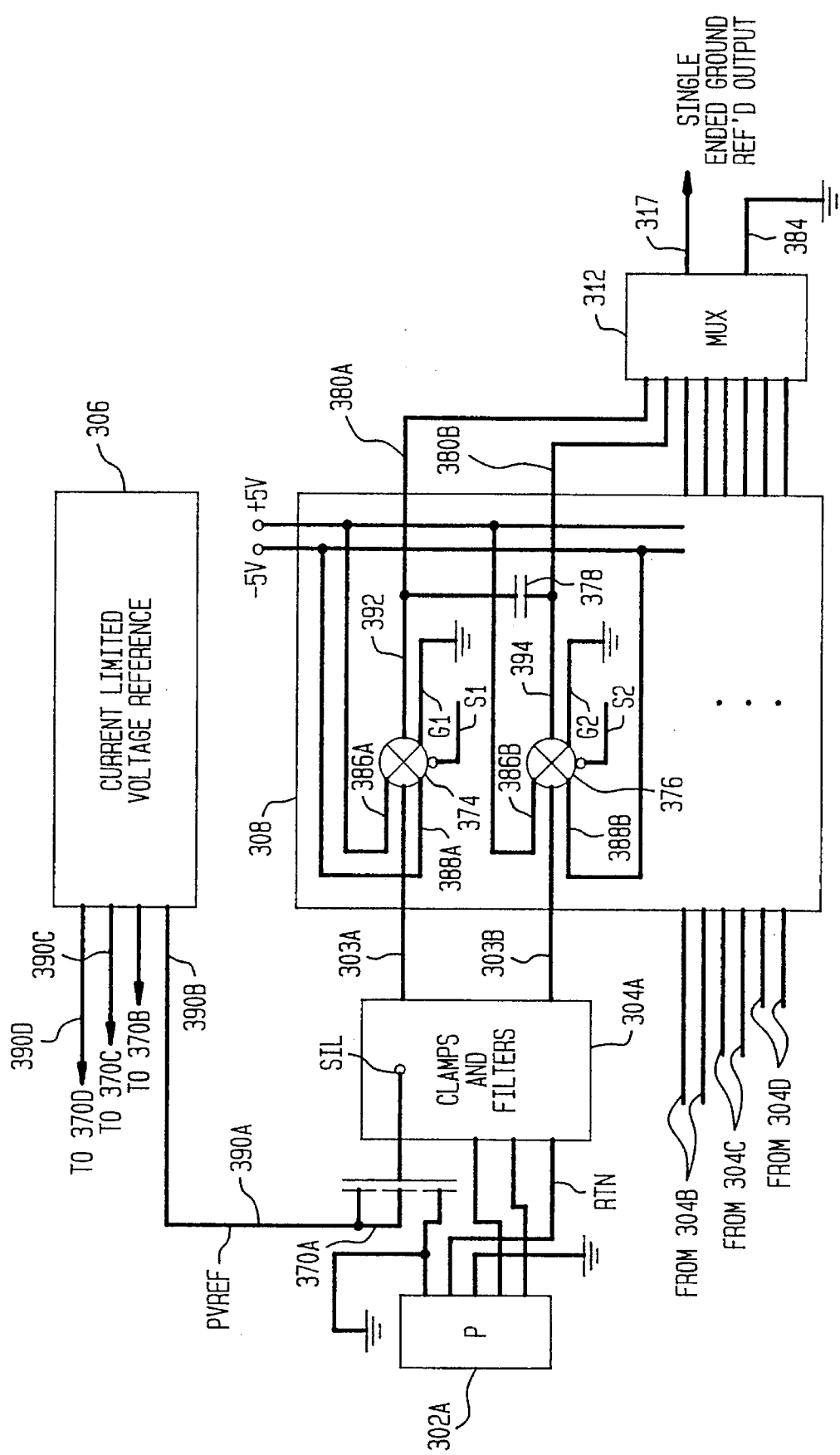
FIG. 7 is a block diagram, partly in schematic diagram form of a differential to single ended converter suitable for use in the data acquisition device shown in FIG. 6.

FIG. 7 shows in greater detail a portion of the circuitry shown in FIG. 6. In particular, details of the differential to single-ended converter 308 are shown. FIG. 7 only shows a single pressure transducer 302a, and its associated circuitry including: clamp and filter network 304a, switch 370a, and electrical paths 303a and 303b, 380a and 380b, and 390a. It is understood by one skilled in the art that these elements and electrical paths are replicated for each of the four transducer data acquisition circuits shown in FIG. 6.

For converting the voltage signal provided by transducer 302a from a differential signal to a single-ended signal, two switches 374 and 376 control the flow of current from the transducer 302a. Switches 374 and 376 receive power from lines 386a, 386b, 388a and 388b. One terminal of transducer 302a is coupled to switch 374 and the other to switch 376. The differential output voltages 392 and 394 from respective switches 374 and 376 are applied across capacitor 378. Switches 374 and 376 receive control signals S1 and S2 from logic circuit 324 (shown in FIG. 6). When signals S1 and S2 are set to their low voltage values, respective switches 374 and 376 are closed, applying the differential voltage signal across capacitor 378. When signals S1 and S2 are set to their high values, the switches are opened and capacitor 378 retains the differential voltage.

Figure 8:
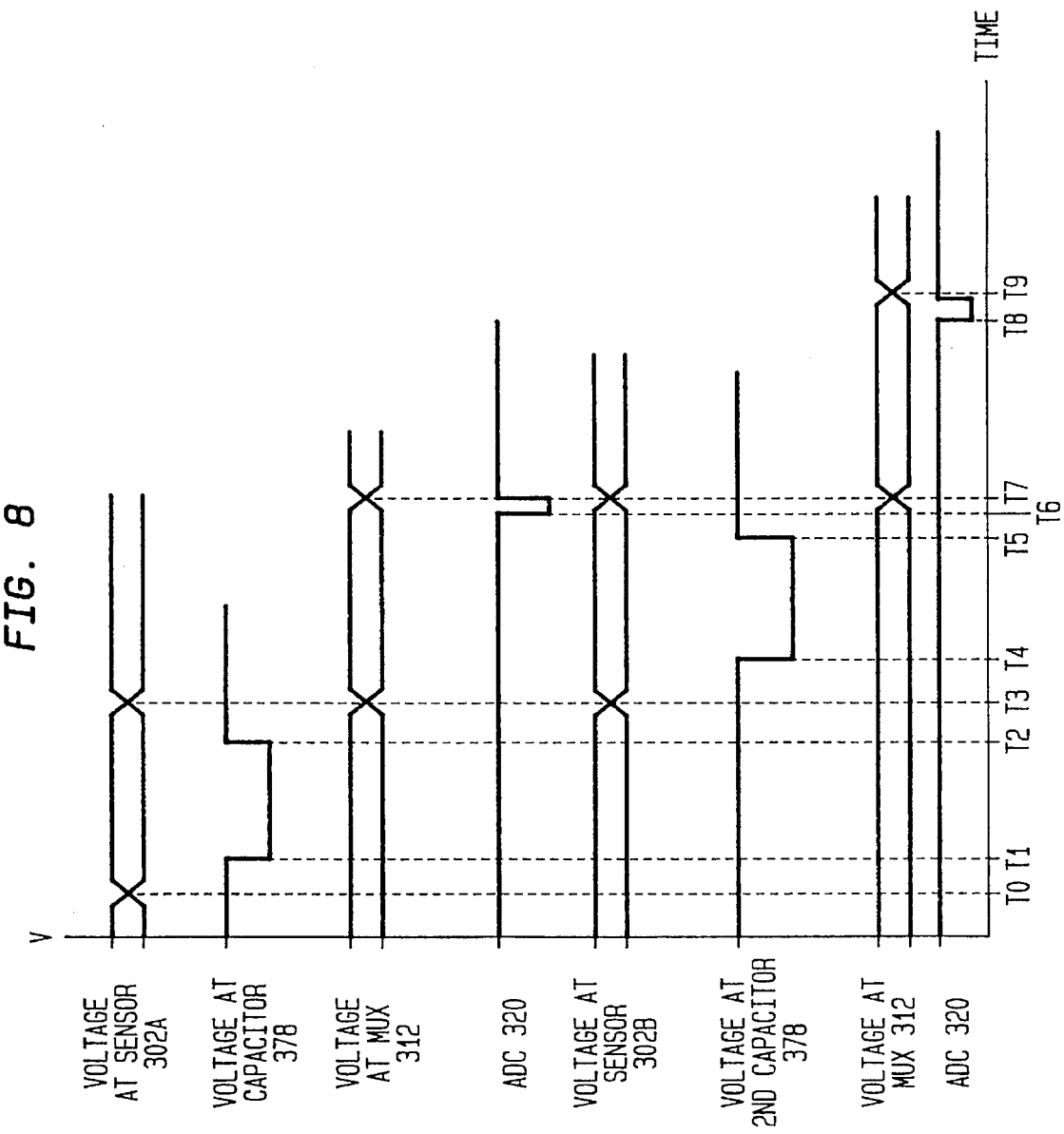
FIG. 8 is a timing diagram which is useful for describing the operation of the data acquisition device shown in FIGS. 2 and 6.

The operation of differential to single-ended converter 308 is shown in FIG. 8. FIG. 8 is a timing diagram which shows the sampling of pressure data from two of the pressure transducers 302a and 302b. It is understood that the data shown represent only one half of a complete cycle for multiplexer 312. That is, the time between T0 and T8 is 3 milliseconds, or three 1-millisecond time slots. An additional 2 milliseconds pass before the output signal of the fourth transducer 302d is sampled by A/D converter 320 (shown in FIG. 6). The temporal relationships between the activation of the second and third transducers 302b and 302c are the same as the temporal relationships between activation of the first and second pressure transducers 302a and 302b. The same temporal relationships apply between the activation of the third and fourth transducers 302c and 302d. And finally, the same temporal relationships apply between the activation of the fourth transducer 302d and activation of the first transducer 302a during the next subsequent cycle of transducer data sampling by multiplexer 312.

Beginning at time T0, switch 370a is closed, thereby applying excitation voltage PVREF to transducer 302a. Switch 370a remains closed for 1 millisecond, until T3. At T1, approximately 15 microseconds after T0, switches 374 and 376 are both closed, coupling capacitor 378 to the differential voltage across the output of transducer 302a, (between lines 392 and 394). Capacitor 378 charges up to the transducer output voltage through the equivalent series output impedance of transducer 302a. Capacitor 378 and the output impedance of transducer 302a form a resistance-capacitance (RC) network which filters noise during the period between T1 and T2, when capacitor 378 is charging.

T2 occurs 15 microseconds before the end of the first time slot. At T2, switches 376 and 378 are opened, decoupling capacitor 378 and transducer 302a. 15 microseconds after T2, at T3, differential multiplexer 312 couples capacitor 378 to the input of amplifier 318 (shown in FIG. 6) via a single ended ground referenced output line 317. The differential voltage on capacitor 378 is thus transformed into a single-ended voltage. During this process, common mode noise voltage is removed. Multiplexer 312 samples the voltage across capacitor 378 until T7, which is 1 millisecond after T3.

During the second time slot, (specifically, between T3 and T7), the output signal on line 317 is amplified by amplifier 318 (shown in FIG. 6) and is transmitted to A/D converter 320 (shown in FIG. 6). A/D converter 320 does not begin sampling immediately at T3. Instead, there is a suitable settling time between T3 and T6 before A/D converter 320 samples the output signal 319 of amplifier 318.

The excitation of, and data gathering from the transducers are pipelined. As each transducer 302a–302d charges a capacitor in converter 308, the voltage from the last previously charged capacitor is amplified and sampled. Thus, during the second time slot, between T3 and T6, switch 370b is closed, activating transducer 302b. At T4, a further pair of switches (not shown) are closed to apply a voltage representing the voltage across transducer 302b, to a further capacitor (not shown). Between T5 and T7, the further pair of switches are opened. During the third time slot, the voltage across the further capacitor is sampled by multiplexer 312 between T7 and T9, and digitized by A/D converter 320 between T8 and T9.

It is understood by one skilled in the art that an excitation voltage is applied to the third transducer 302c during the third time slot and its output signal is digitized during the fourth time slot. The excitation voltage is applied to the fourth transducer 302d during the fourth time slot and its output signal is digitized during the fifth time slot. The excitation voltage is applied to the first transducer 302a again during the fifth time slot and its output signal is digitized during the sixth time slot.

The circuit topology described above has several advantageous aspects. Power consumption is low, because the reference voltage is only applied to one transducer at a time. A single current limited voltage reference is shared by the four transducers 302a–302d, which may reduce costs. The circuit described above has low susceptibility to noise that is common mode in nature. This is particularly important in a hospital setting, where electro-surgery units (ESU) often produce a high frequency common mode noise signal. Unlike the differential instrumentation amplifiers typically used in prior art cartridges, the circuitry shown in FIGS. 6 and 7 has a high common mode rejection ratio that is essentially independent of frequency. The differential instrumentation amplifiers used in these prior art cartridges typically have lower common mode rejection for high frequency noise signals (such as those produced by ESUs) than for low frequency noise signals.

The current limited voltage reference 306 provides a reference voltage to one of the transducers 302a–302d at a time, during its respective time slot. Voltage reference 306 includes means to sense when one of the transducers 302a–302d has developed a short circuit. Voltage reference 306 will not deliver current in excess of a predetermined limit, to protect the patient and the equipment from further damage. In such a condition, the voltage reference signal 390a–390d for the failed transducer 302a–302d is held to the predetermined current limit each time device 30 attempts to apply an excitation voltage to the failed transducer. Voltage reference 306 is able to stabilize at the predetermined current limit during the 15 microsecond period between closing switch 370a–370d and closing switches 374 and 376 to apply voltage to capacitor 378. Voltage reference 306 is also able to return to the desired reference voltage during the same 15 microsecond period before the switches are closed to apply the differential voltage from the next transducer.

Referring again to FIG. 6, there is also shown circuitry for receiving and processing signals representing temperature from temperature sensors 350a and 350b. The temperatures signals are conditioned by filters 352a and 352b. The filtered signals are multiplexed together in a multiplexer 356. A multiplexed signal is provided to A/D converter 320 to provide a single digital temperature signal 322.

Although the exemplary embodiments include data acquisition devices 30 adapted to receive up to four transducers, it is understood that devices in accordance with the invention may be constructed for use with a different number of transducers.

It is understood by one skilled in the art that many variations of the embodiments described herein are contemplated. While the invention has been described in terms of exemplary embodiments, it is contemplated that it may be practiced as outlined above with modifications within the spirit and scope of the appended claims.

What is claimed:

1. A data acquisition device located in a first housing for use in a patient monitoring area having a patient monitoring system located therein for monitoring a patient, which patient monitoring system includes a signal processing and display device located in a second housing which is remote and independently positionable from said first housing, but still located in said patient monitoring area, and a plurality of pressure transducers adapted to be coupled to a patient, said transducers producing a plurality of patient blood pressure signals, the data acquisition device comprising:

receiving means in said first housing for receiving signals representing blood pressure from said plurality of pressure transducers;

conditioning means, coupled to said receiving means, located in said first housing, and responsive to control signals from said signal processing and display device for controllably conditioning the signals representing blood pressure for transmission to the signal processing and display device, the pressure transducers and the conditioning means being collocated, and the conditioning means, due to being located in said first housing, being positionable independent of the signal processing and display device located in said second housing;

means for electrically coupling the pressure transducers with the conditioning means; and bi-directional communication means for selectively coupling the conditioning means with the signal processing and display device, to provide for the transmission of said control signals from said signal processing and display device located in said second housing to said data acquisition device located in said first housing for controlling said conditioning means, and to provide for the transmission of the conditioned blood pressure signals from said first housing to the signal processing and display device in said second housing.

2. A data acquisition device in accordance with claim 1, wherein said first housing includes means for detachably mounting the pressure transducers to the first housing.

3. A device in accordance with claim 2, wherein the receiving means includes a connector which is collocated with the means for detachably mounting.

4. A device in accordance with claim 2, wherein the means for detachably mounting includes a channel in the first housing, the channel being sized to receive a mounting apparatus of the transducers.

5. A device in accordance with claim 4, wherein the mounting means includes a transducer holder having a further channel therein sized to receive the transducers, and wherein the channel in the first housing is sized to receive the holder.

6. A device in accordance with claim 2, further comprising a switch located on the first housing and coupled to said bi-directional communication means to transmit a pressure zero signal to the display device, to cause the display device to associate the conditioned signal received from said conditioning means to a waveform display value of zero.

7. A device in accordance with claim 2, further comprising a switch located on the first housing which transmits a pressure zero signal to the display device, to cause the display device to associate the conditioned signal received from said conditioning means to a waveform display value of zero.

8. A device in accordance with claim 2, further comprising a switch located on the first housing which transmits a wedge start signal to the display device, to cause the display device to initiate a pulmonary artery wedge measurement procedure.

9. A device in accordance with claim 1, further comprising means for positioning the device at various heights relative to the patient.

10. A device in accordance with claim 9, wherein the positioning means include means for mounting the first housing on an intravenous pole.

11. A device in accordance with claim 9, wherein the positioning means include means for mounting the first housing on a bed.

12. A device in accordance with claim 1, wherein the system includes a plurality of transducers, and the conditioning means includes multiplying means responsive to control signals received via said bi-directional communication means for transmitting signals representing blood pressure received from all of the plurality of transducers over a single cable.

13. A device in accordance with claim 1, wherein the system includes a plurality of transducers, and the conditioning means includes time division multiplex means responsive to said control signals for combining signals representing blood pressure received from all of the plurality of transducers to form a single output signal.

14. A device in accordance with claim 13, wherein the conditioning means includes switch means responsive to said control signals for selectively activating said plurality of transducers one at a time.

15. A device in accordance with claim 1, wherein the signals representing blood pressure are differential voltage signals, and the conditioning means include means responsive to said control signals for converting the differential voltage signals to single-ended voltage signals.

16. A device in accordance with claim 1, further comprising means responsive to said control signals for applying a reference voltage signal having a predetermined voltage value and a predetermined current value to the transducers, including means for maintaining the current value of the reference voltage signal below a predetermined limit.

17. A device in accordance with claim 1, further comprising a memory associated with the first housing for storing data which include pressure transducer calibration data and alarm limits.

18. A device in accordance with claim 17, wherein the transducer electrical coupling means include a cable, and wherein the memory is attached to the cable.

* * * * *